United States Patent
Huang et al.

(10) Patent No.: US 9,821,017 B2
(45) Date of Patent: Nov. 21, 2017

(54) **EXTRACT OF *ASPLENIUM NIDUS* L**

(71) Applicants: JIN XIN BIOTECHNOLOGY CO., LTD., Kaohsiung (TW); ACADEMIA SINICA, Taipei (TW)

(72) Inventors: Kun-Hsuan Huang, Kaohsiung (TW); Tza-Zen Chaung, Kaohsiung (TW); Pei-Wen Hsiao, Kaohsiung (TW); Chia-Jui Tsai, Kaohsiung (TW)

(73) Assignees: Jin Xin Biotechnology Co., Ltd., Kaohsiung (TW); Academia Sinica, Taipei (TW)

( * ) Notice: Subject to any disclaimer, the term of this patent is extended or adjusted under 35 U.S.C. 154(b) by 315 days.

(21) Appl. No.: 14/665,538

(22) Filed: Mar. 23, 2015

(65) Prior Publication Data
US 2015/0190441 A1  Jul. 9, 2015

Related U.S. Application Data

(62) Division of application No. 13/929,444, filed on Jun. 27, 2013, now Pat. No. 9,056,077.

(30) Foreign Application Priority Data

Jun. 27, 2012 (TW) ............... 101123087 A
Jun. 26, 2013 (TW) ............... 102122748 A

(51) Int. Cl.
| | |
|---|---|
| *A61K 36/11* | (2006.01) |
| *A61K 36/185* | (2006.01) |
| *A61K 36/12* | (2006.01) |
| *A61K 31/231* | (2006.01) |
| *A61K 31/232* | (2006.01) |
| *A61K 31/409* | (2006.01) |
| *A61K 31/23* | (2006.01) |
| *A23L 33/105* | (2016.01) |

(52) U.S. Cl.
CPC ............ *A61K 36/12* (2013.01); *A23L 33/105* (2016.08); *A61K 31/23* (2013.01); *A61K 31/231* (2013.01); *A61K 31/232* (2013.01); *A61K 31/409* (2013.01); *A23V 2002/00* (2013.01)

(58) Field of Classification Search
None
See application file for complete search history.

(56) References Cited

U.S. PATENT DOCUMENTS

| 7,069,690 | B2 * | 7/2006 | Ma .................... A01H 9/00 210/602 |
|---|---|---|---|
| 7,250,182 | B2 | 7/2007 | Dong |
| 2004/0144155 | A1 * | 7/2004 | Ma .................... A01H 9/00 47/58.1 R |
| 2010/0204319 | A1 | 8/2010 | Archibald |

FOREIGN PATENT DOCUMENTS

| JP | 2003-113064 | 4/2003 |
|---|---|---|
| JP | 2004-123657 | 4/2004 |

OTHER PUBLICATIONS

How Yee Lai, Yau Yan Lim & Shiau Pin Tan, "Antioxidative, Tyrosinase Inhibiting and Antibacterial Activities of Leaf ,Extracts from Medicinal Ferns", Bioscience, Biotechnology, and Biochemistry, Jun. 7, 2009, p. 1362-1366, United Kingdom.
Lih-Shiuh Lai, Hui-Yuan Liang, "Chemical compositions and some physical properties of the water and alkali-extracted mucilage from the young fronds of Asplenium australasicum (J. Sm.) Hook", Food Hydrocolloids, 2012, p. 344-349, Taiwan, ROC.
Chen Qing-yu, Kou Dong-quan, Wang Wei, Zhang Wei, Cheng Shao-wen, Lin Zhong-qin, Lu Chuan-zhu and Peng Lei, "Effects of water extract of neottopteris nidus on osteoblasts", Shanghai Journal of traditional Chinese Medicine, Aug 2011, p. 69-72, Hollande.
Filippo Imperalo, "A new flavonal glycoside from the fern *Asplenium nidus*", Chemistry & Industry, Jul. 20, 1987, p. 487, No. 14, London.
Filippo Imperato, "An unusual glycosylation pattern in a new flavonoid from the fern *Asplenium nidus*", Chemistry and Industry, Aug. 18, 1986, p. 555, Italy.

* cited by examiner

*Primary Examiner* — Chris R Tate
*Assistant Examiner* — Randall Winston
(74) *Attorney, Agent, or Firm* — Muncy, Geissler, Olds & Lowe, P.C.

(57) ABSTRACT

An extract of *Asplenium nidus* L. includes pyropheophorbide a methyl ester ($C_{34}H_{36}N_4O_3$), pheophorbide a methyl ester ($C_{35}H_{36}N_4O_5$), 1-linleoyl-3-linolenoyl-glycerol ($C_{39}H_{66}O_5$), 1-linleoyl-2,3-dipalmitoyl-rac-glycerol ($C_{53}H_{98}O_6$) and 1,3-dipalmitoyl-sn-glycerol ($C_{35}H_{68}O_5$). The extract of *Asplenium nidus* L. is obtained by using a method including steps of: solvent extraction, using an solvent to extract an *Asplenium nidus* L. sample and to obtain an extract, with a w/v ratio between the solvent and the *Asplenium nidus* L. sample being 50~60 mg/ml; and column chromatography, fractionating the extract with water and ethanol as eluent to obtain several fractions including fraction a to fraction i, and further evaporating and lyophilizing fraction b, c, d or their combination to obtain an extract of *Asplenium nidus* L.

8 Claims, 13 Drawing Sheets
(1 of 13 Drawing Sheet(s) Filed in Color)

EXTRACT OF *ASPLENIUM NIDUS* L

This is a divisional application of U.S. patent application Ser. No. 13/929,444 filed on Jun. 27, 2013.

BACKGROUND OF THE INVENTION

1. Field of the Invention

The present invention generally relates to an extract of herbal and, more particularly, to an extract of *Asplenium nidus L.* apt to treat of prostate diseases.

2. Description of the Related Art

Prostate, located around bladder outlet and surrounded by urethra, is a part of male's reproductive system.

Benign prostate hyperplasia (BPH) refers to hyperplasia of prostate stromal and epithelial cells, and generally occurs on male in fifty, usually resulting in the formation of large, fairly discrete nodules in the periurethral region of the prostate. Progress of the benign prostate hyperplasia is unknown so far. Instead, it is believed androgens (testosterone and related hormones) and ages play a permissive role in the occurrence of the benign prostate hyperplasia. When suffering from the benign prostate hyperplasia, enlargement of prostate will compress the urethral canal to cause partial or sometimes virtually complete obstruction of the urethra, and thus, interfering with normal flows of urine and leading to voiding dysfunctions, such as interruption, urorrhagia, incontinence and residual urine. Seriously, it may also lead to uremia or renal failure. Although benign prostate hyperplasia may not increase incidence to prostate cancer, it usually causes false positive in the diagnosis of prostate cancer due to similar symptoms among each other, and accordingly deferring a preferable time for treatment, or affecting patient's mood somehow.

A conventional therapy of benign prostate hyperplasia generally depends on surgery or drug, but primary on drug treatment due to the prognosis and risk of surgery. Conventional drugs for benign prostate hyperplasia include alpha adrenergic blockers, such as Minipress, Dibenyline, Hytrin, Doxaben, and Xatral, and hormone inhibitor. However, the said conventional drugs may lead to some side effects, such as hypotension, incontinence, nasal congestion, fatigue, and sexual dysfunction, and even lead to complications as cooperating with other drugs (medicines for common cold, cardiovascular disease, and hypertension, for example), bringing about unbearable illness to patients. Furthermore, in view of researches, it may increase the incidence to prostate cancer and breast cancer after taking the said drugs for a long-term.

Recently, traditional medicine (TM) and complementary and alternative medicine (CAM) has getting popular and important in Europe and United States, and accordingly, traditional herbs having therapeutic effects on prostate diseases, including lycopene, pumpkin seeds, saw palmetto, *Pygeum africana*, and progesterone, are gradually reported and developed. However, most of the said herbs are limited in use due to their inefficient effects (as an example, lycopene and pumpkin seeds being less effective in the therapy of prostate disease), poor extraction rate or origins (saw palmetto and *Pygeum africana* being difficult to obtain, as being available in Africa, and coast of Atlantic and Caribbean only). Also, similar to the said drugs, the said traditional herbs will cause some side effects, stomach discomfort, nausea, constipation or diarrhea caused by saw palmetto (reference being available at: http://liaozhai.pujia-.com/thread-500003-1.html) for instance. In such, the said traditional herbs are limited in practical use.

Hence, it is needed to provide a new herbal product, having significantly therapeutic effects on prostate diseases, and capable of being further developed in clinical therapy or prophylaxis of prostate diseases.

*Asplenium nidus L.* is a species of fern in the family Aspleniaceae, native to tropical southeastern Asia, eastern Australia, Hawaii, Polynesia, Christmas Island, India, and eastern Africa. Recently *Asplenium nidus L.* has been widely cultivated and developed in Taiwan. Generally, *Asplenium nidus L.* is commonly sold as house plants, being a vegetable rich in various nutrients and dietary fibers, and also it has been used locally in folk medicine to prevent from hypertension, asthma, diabetes, constipation and colorectal cancer. Yet, a therapeutic use of *Asplenium nidus L.* on prostate diseases has not been well-studied and reported.

SUMMARY OF THE INVENTION

It is therefore the objective of this invention to provide an extract of *Asplenium nidus L.*, which comprises natural active substances against to androgen, and is apt to treat of prostate disease.

It is therefore the further objective of this invention to provide an extract of *Asplenium nidus L.*, capable of modulating the secretion of androgen. The said extract of *Asplenium nidus L.* is easy to obtain and to isolate, so that it can be further applied to pharmaceutical industry, as an active substance in medications or health products for prostate disease.

It is therefore the further objective of this invention to provide an extract of *Asplenium nidus L.*, putting in use on therapy or prophylaxis of prostate disease.

An extract of *Asplenium nidus L.* comprises pyropheophorbide a methyl ester, pheophorbide a methyl ester, 1-linleoyl-3-linolenoyl-glycerol, 1-linleoyl-2,3-dipalmitoyl-rac-glycerol and 1,3-dipalmitoyl-sn-glycerol.

The said extract of *Asplenium nidus L.* is obtained by using a method comprising: solvent extraction, by extracting a sample of *Asplenium nidus L.* with a solvent, with a w/v ratio of the sample of *Asplenium nidus L* and the solvent being 50-60 mg/ml, and obtaining an extract; column chromatography, by fractionating the extract using a silica gel column chromatography and using water and ethanol as eluents to obtain several fractions, being fraction a to fraction i sequentially; and further evaporating and lyophilizing fraction c to obtain an extract of *Asplenium nidus L.*

In the extract of *Asplenium nidus L.*, fraction b is evaporated and lyophilized to obtain the extract of *Asplenium nidus L.*

In the extract of *Asplenium nidus L.*, fraction d is evaporated and lyophilized to obtain the extract of *Asplenium nidus L.*

In the extract of *Asplenium nidus L.*, the solvent is 95% alcohol.

In the extract of *Asplenium nidus L.*, the solvent is water.

The said extract of *Asplenium nidus L.* is obtained by using the method further comprising a step of selecting, by selecting the whole plant of *Asplenium nidus L.* as the sample of *Asplenium nidus L.*

In the extract of *Asplenium nidus L.*, the whole plant of *Asplenium antiquum* Makino is selected as the sample of *Asplenium nidus L.*

In the extract of *Asplenium nidus L.*, the whole plant of *Asplenium nidus* Linn is selected as the sample of *Asplenium nidus L.*

The said extract of *Asplenium nidus L.* is used on pharmaceutical industry as an active substance treated of prostate disease, with the prostate disease comprising benign prostate hyperplasia, prostate cancer or prostatitis, with an effective amount of the extract of *Asplenium nidus L.* is 10 to 50 mg/kg of body weight of a subject in need.

The said extract of *Asplenium nidus L.* is used on manufacture of health products as an active substance treated of prostate disease, with the prostate disease comprising benign prostate hyperplasia, prostate cancer or prostatitis, with an effective amount of the extract of *Asplenium nidus L.* is 10 to 50 mg/kg of body weight of a subject in need.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given hereinafter and the accompanying drawings which are given by way of illustration only, and thus are not limitative of the present invention, and wherein.

Figure 1:
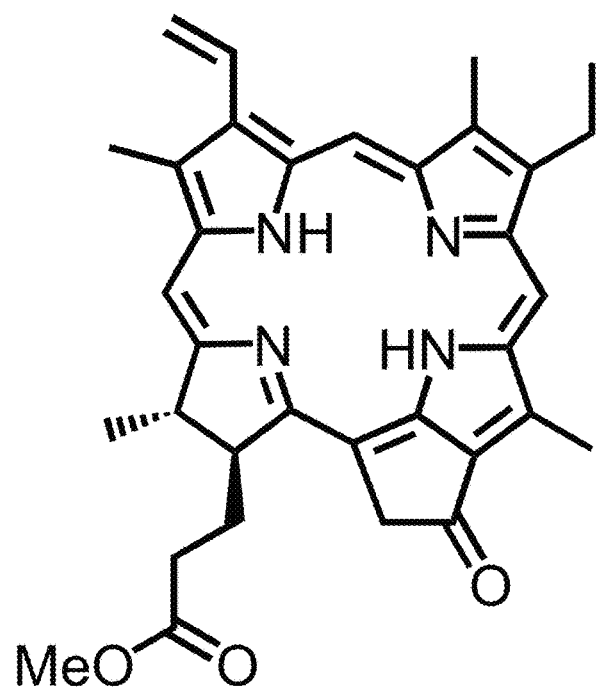
FIG. 1 is a diagram illustrating the chemical structure of pyropheophorbide a methyl ester.

In the various figures of the drawings, the same numerals designate the same or similar parts. Furthermore, when the terms "first", "second", "third", "fourth", "inner", "outer" "top", "bottom" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

Figure 2:
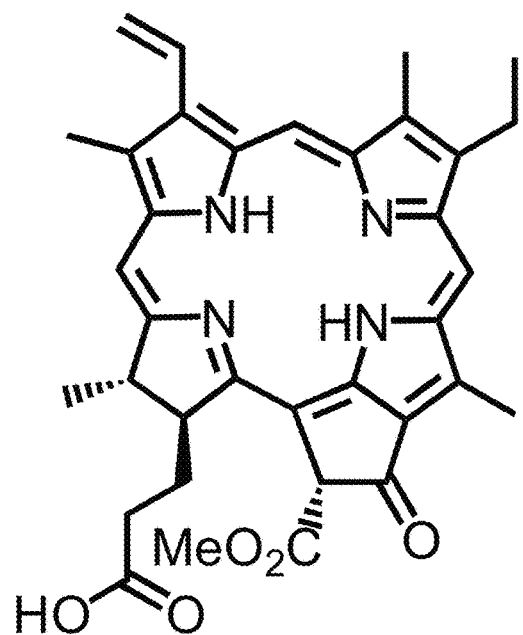
FIG. 2 is a diagram illustrating the chemical structure of pheophorbide a methyl ester.
Figure 3:
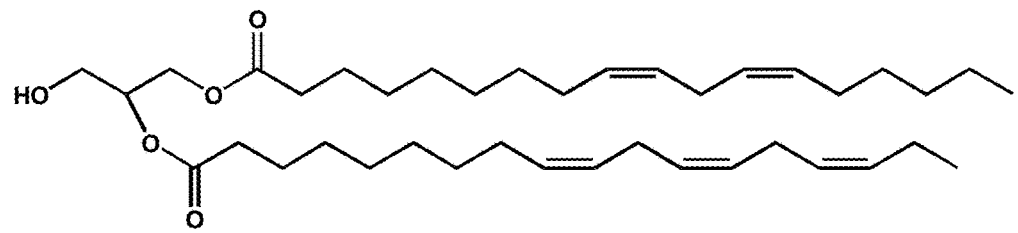
FIG. 3 is a diagram illustrating the chemical structure of 1-linleoyl-3-linolenoyl-glycerol.
Figure 4:
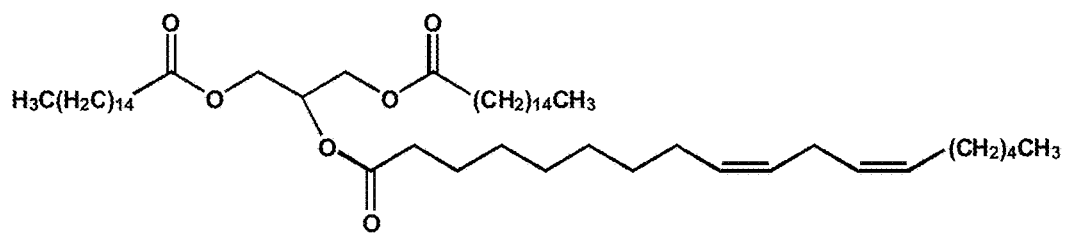
FIG. 4 is a diagram illustrating the chemical structure of 1-linleoyl-2,3-dipalmitoyl-rac-glycerol.
Figure 5:
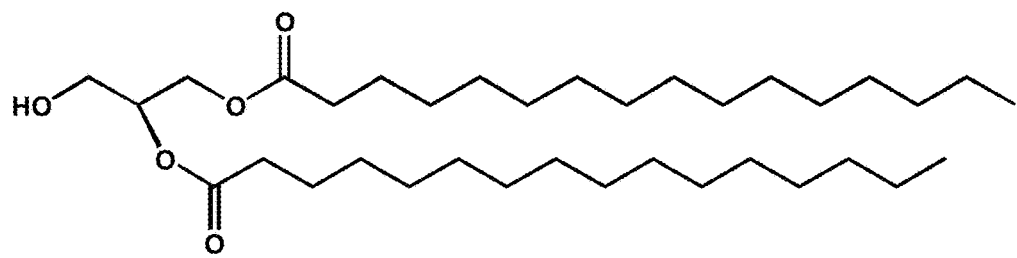
FIG. 5 is a diagram illustrating the chemical structure of 1,3-dipalmitoyl-sn-glycerol.

With reference to FIGS. 1 and 2, a preferred embodiment of the invention discloses an extract of *Asplenium nidus L.* comprising pyropheophorbide a methyl ester ($C_{34}H_{36}N_4O_3$; as shown in FIG. 1), pheophorbide a methyl ester ($C_{35}H_{36}N_4O_5$; as shown in FIG. 2), 1-linleoyl-3-linolenoyl-glycerol ($C_{39}H_{66}O_5$, as shown in FIG. 3), 1-linleoyl-2,3-dipalmitoyl-rac-glycerol ($C_{53}H_{98}O_6$, as shown in FIG. 4) and 1,3-dipalmitoyl-sn-glycerol ($C_{35}H_{68}O_5$, as shown in FIG. 5) and the said extract of *Asplenium nidus L.* is capable of inhibiting the secretion of androgen, decreasing inflammatory and reducing incidence to prostate disease.

Figure 6:
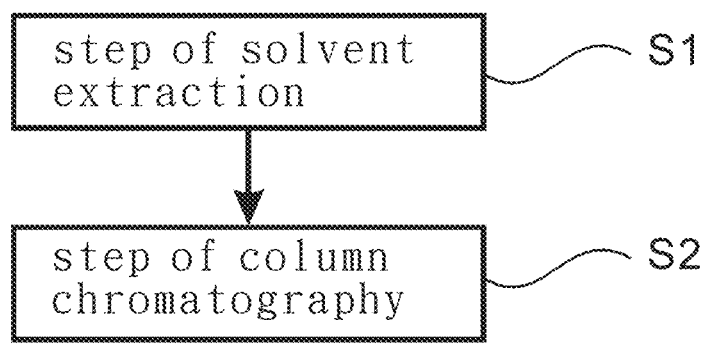
FIG. 6 is a diagram illustrating an extracting method of an extract of *Asplenium nidus L.* in a preferable embodiment of the present invention.

FIG. 6 shows an extracting method of the extract of *Asplenium nidus L.* of the preferable embodiment in the present invention, comprising steps of solvent extraction S1 and column chromatography S2.

In the step of solvent extraction S1, a sample of *Asplenium nidus L.* is prepared and extracted with a solvent, with a w/v ratio of the sample of *Asplenium nidus L.* and the solvent being 50-60 mg/ml, to obtain an extract, wherein the solvent is 95% alcohol.

In the step of column chromatography, the said extract is fractioned by using a silica gel column chromatography, with water and alcohol being eluents, to obtain several fractions, including fractions a to i by order of elution, and then fractions b, c, d or their combination is selected, evaporated, and lyophilized to obtain the extract of *Asplenium nidus L.* of the preferable embodiment of the present invention.

Figure 7:
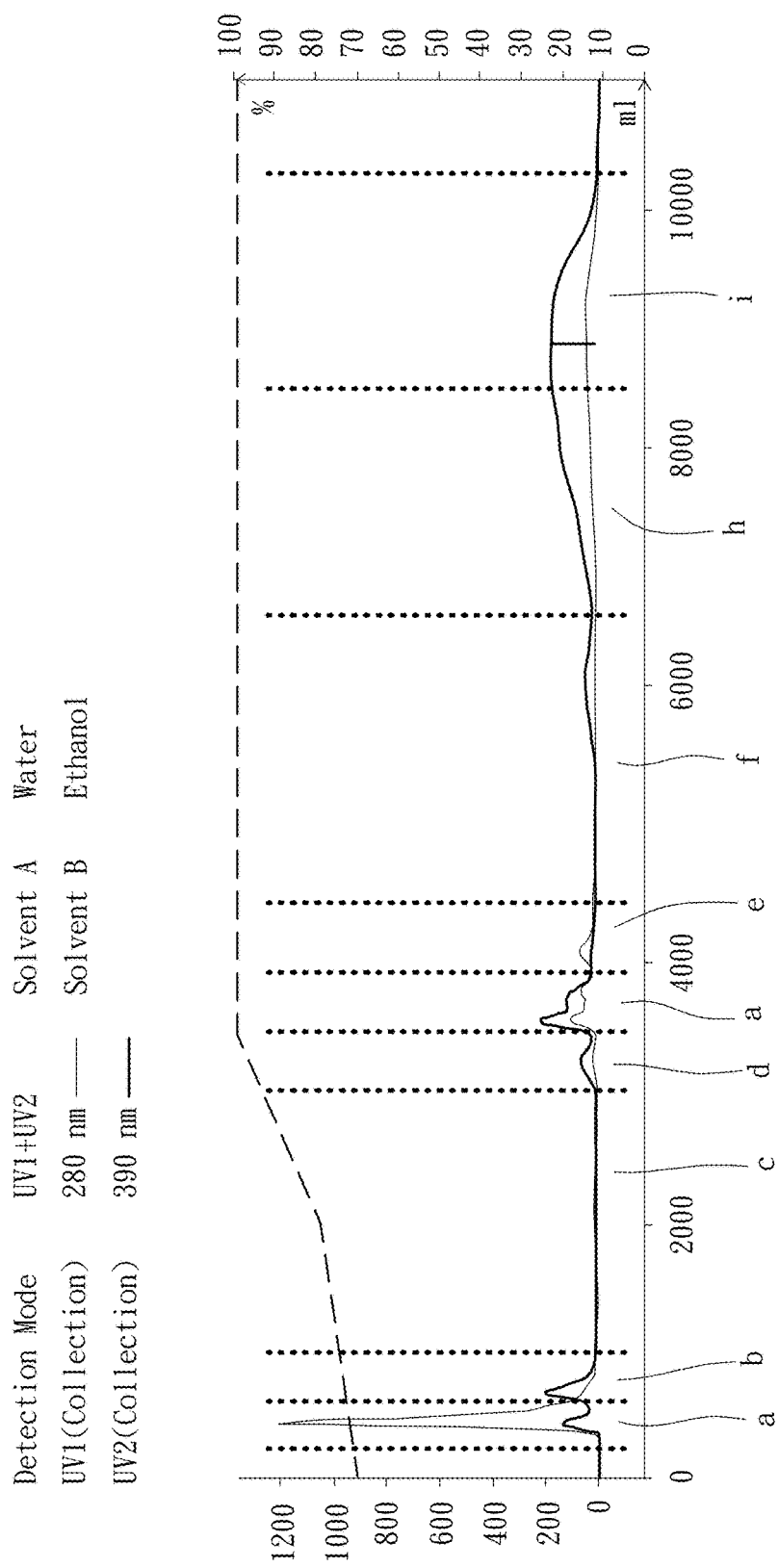
FIG. 7 is a diagram illustrating eluting fractions of an extract of *Asplenium nidus L.* in a preferable embodiment of the present invention.

Precisely, elution in the step of column chromatography is carried out via an automated middle-sized liquid chromatography-Flash LC, preferably with reverse phase column C18, to achieve preferable extracting rate, followed by using eluents in various compositions to obtain several fractions, as shown in FIG. 7. The several fractions comprising fractions a, b, c, d, e, f, g, h, i by the order of elution are successfully obtained. Finally, the fractions b, c, d or their combination are selected, evaporated and lyophilized to obtain the extract of *Asplenium nidus L.* of the preferable embodiment in the present invention. The said eluents comprise alcohol and water mixed with each other in a linear gradient, wherein a concentration of alcohol in the eluents varies from 70% to 100%.

Figure 8:
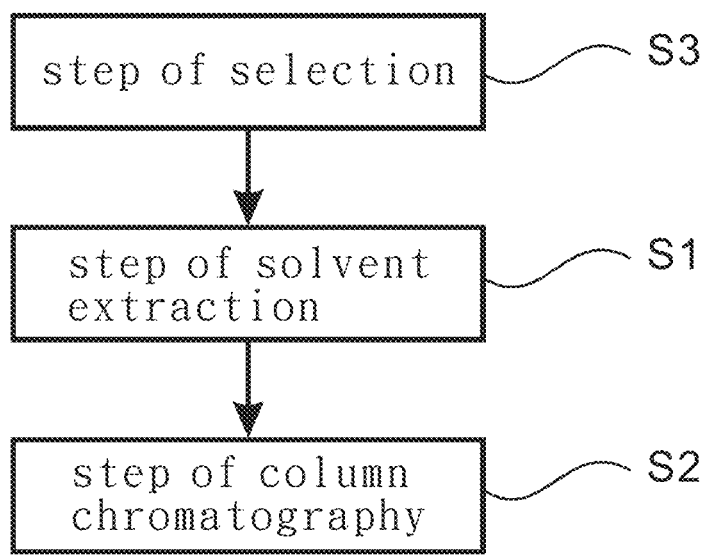
FIG. 8 is diagram illustrating another extracting method of an extract of *Asplenium nidus L.* in a preferable embodiment of the present invention.

With reference to FIG. 8, the extracting method of the extract of *Asplenium nidus L.* of the preferable embodiment in the present invention preferably comprises a step of selection S3 before the step of solvent extraction S1, with the sample of *Asplenium nidus L.* being selected as a whole plant of *Asplenium nidus L.* (including roots), so that, an extract of *Asplenium nidus L.* having a great amount of active substance is successfully obtained. Furthermore, the sample of *Asplenium nidus L.* is selected from a whole plant of *Asplenium antiquum* Makino or *Asplenium nidus* Linn, preferably a whole plant of *Asplenium nidus* Linn including roots. Since, *Asplenium nidus* Linn is commonly distributed and cultivated throughout Taiwan, throughout the year, it is easy to obtain the sample of *Asplenium nidus L.* and further to use in the extracting method of the present invention. Also, the *Asplenium nidus* Linn is green and organic vegetables, being free from contamination of pesticide and insects, so that the food safety thereof can be guarantee.

It is demonstrated that the extract of *Asplenium nidus L.* has active substances (including pyropheophorbide a methyl ester, pheophorbide a methyl ester, 1-linleoyl-3-linolenoyl-glycerol, 1-linleoyl-2,3-dipalmitoyl-rac-glycerol and 1,3-dipalmitoyl-sn-glycerol) against androgen and inflammation. Therefore, the said extract of *Asplenium nidus L.* is capable of modulating the secretion of hormone, and further controlling diseases caused by hormone imbalance, such as prostate diseases (including benign prostate hyperplasia, prostate cancer and prostatitis), incontinence, androgenic alopecia and menopausal disorders.

Also, the extract of *Asplenium nidus L.* is easy to obtain and to isolate, capable of being used on pharmaceutical industry, as an active substance in medications or health products for the said disease, the said prostate diseases in particular. The extract of *Asplenium nidus L.* can be used individually, or in combination with pharmaceutical acceptable vehicles, excipients, salts or other nutrients, being in a composite. In addition, the extract of *Asplenium nidus L.* can be further manufactured into any oral type that is easy to take, such as pastil, capsule, powder, pill, solution, or fermented products. Yet, the extract of *Asplenium nidus L.* can be combined with other food products or drinks, being manufactured into a more convenient type for taking.

For proving the extract of *Asplenium nidus L.* in the preferable embodiment of the present invention truly having ability against androgen, a serial of trial is demonstrated below. However, the application of the said extract of *Asplenium nidus L.* is not limited to that.

Figure 9:
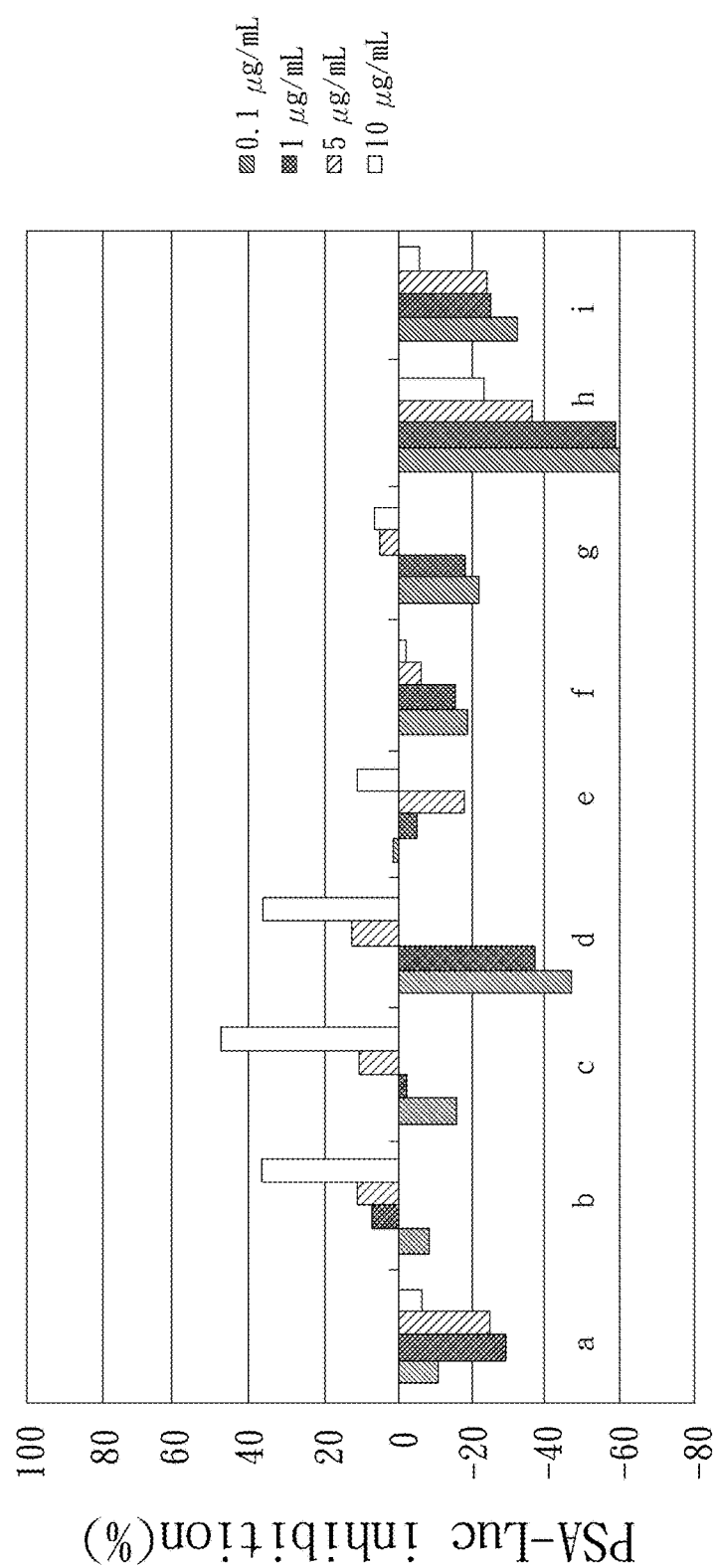
FIG. 9 is a bar chart illustrating the level of PSA-Luc inhibition of an extract of *Asplenium nidus L.* in a preferable embodiment of the present invention.
Figure 10:
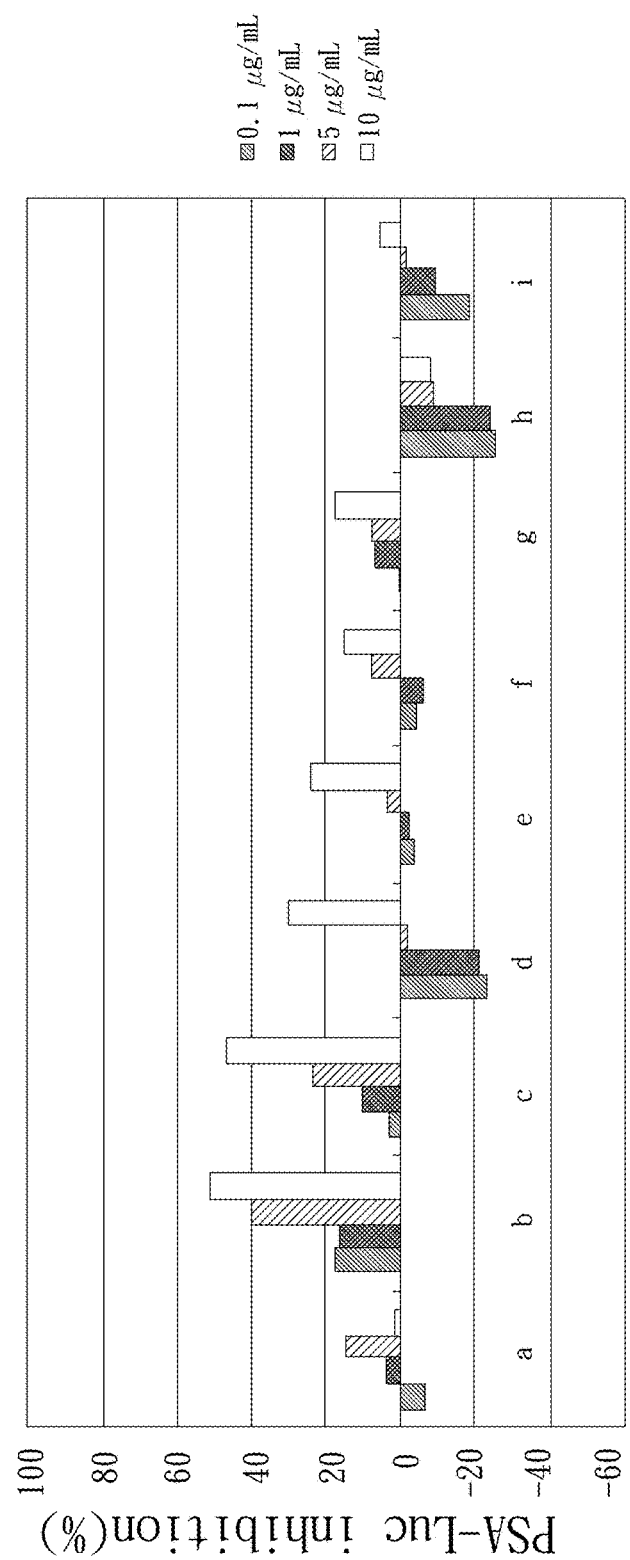
FIG. 10 is another bar chart illustrating the level of PSA-Luc inhibition of an extract of *Asplenium nidus L.* in a preferable embodiment of the present invention.

In the present trial, the said extracting method is carried out by processing the step of selection S3, the step of solvent extraction S1, and the step of column chromatography S2 sequentially, with the sample of *Asplenium nidus L.* being extracted by using 95% alcohol (being the solvent), followed by eluting via the automated middle-sized liquid chromatography-Flash LC (with reverse phase column C18) to obtain 9 fractions (including a to i). With reference to FIGS. 9 and 10, the 11 fractions are collected and cultured with prostate cancer cell line 22Rv/103E respectively, or co-cultured with a mix of the prostate cancer cell line 22Rv/103E and stromal myofibroblast-WPMY-1 respectively, and then activity against androgen of each fraction is determined.

In view of FIGS. 9 and 10, fractions b, c, and d all show significant inhibition either when they are cultured with the prostate cancer cell line 22Rv/103E respectively (see FIG. 9), or are co-cultured with the mix of the prostate cancer cell 22Rv/103E and the stromal myofibroblast-WPMY-1 (see FIG. 10), and particularly in a dose-dependent manner.

Figure 11:
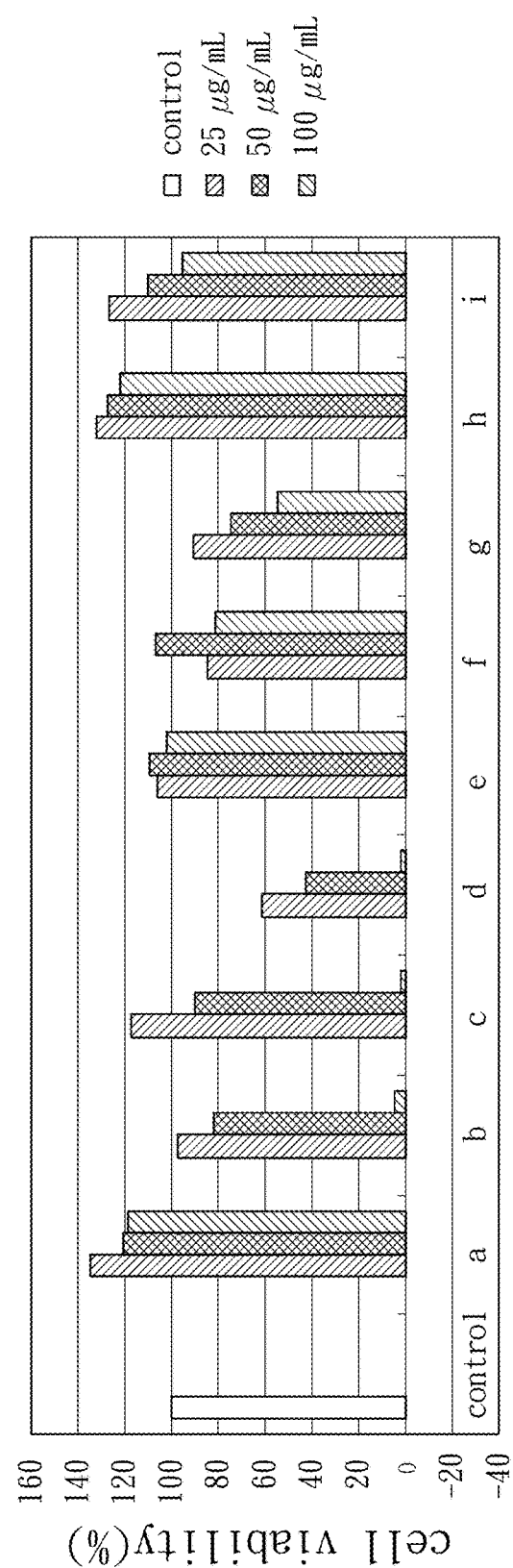
FIG. 11 is a bar chart illustrating cell viability of WPMY-1 after treated with an extract of *Asplenium nidus L.* in a preferable embodiment of the present invention.
Figure 12:
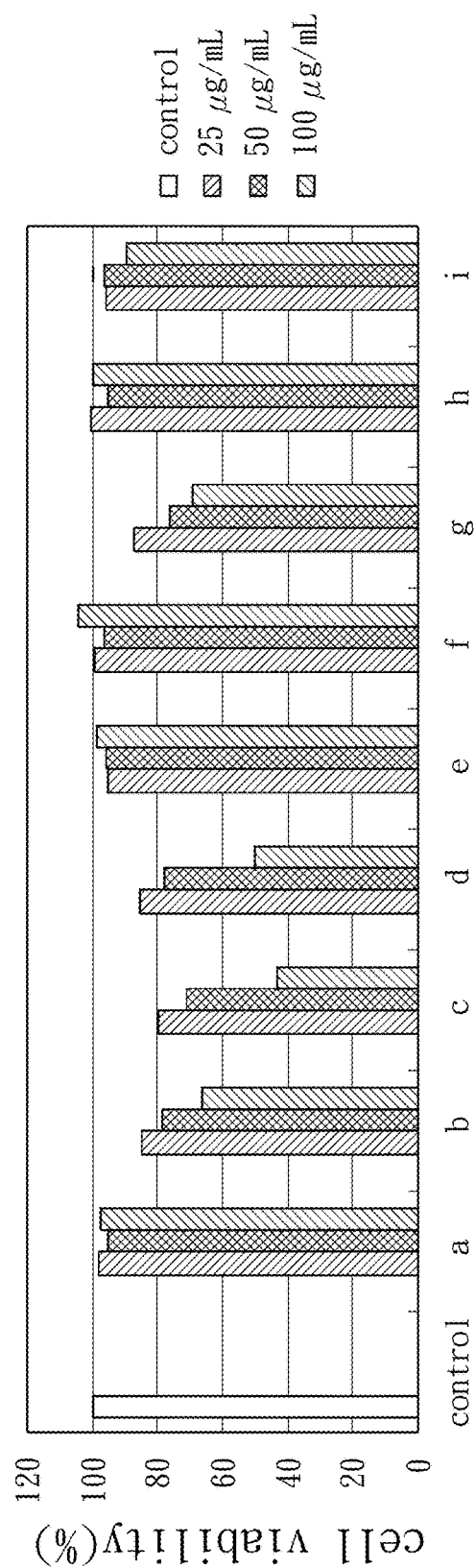
FIG. 12 is a bar chart illustrating cell viability of LNCaP after treated with an extract of *Asplenium nidus L.* in a preferable embodiment of the present invention.

In FIGS. 11 and 12, cell viability of the stromal myofibroblast-WPMY-1 and prostate cancer cell line-LNCaP are demonstrated after culturing with the 9 fractions respectively. The stromal myofibroblast-WPMY-1 and the prostate cancer cell line-LNCaP are cultured with the 9 fractions respectively for 48 hours. After that, the stromal myofibroblast-WPMY-1 and the prostate cancer cell line-LNCaP are dyed with SRB dye, and then the cell viability thereof is determined.

According to FIGS. 11 and 12, the fractions b, c, and d apparently have inhibition on the growth of the stromal myofibroblast-WPMY-1 and the prostate cancer cell line-LNCaP in a dose-depended manner.

Figure 13:
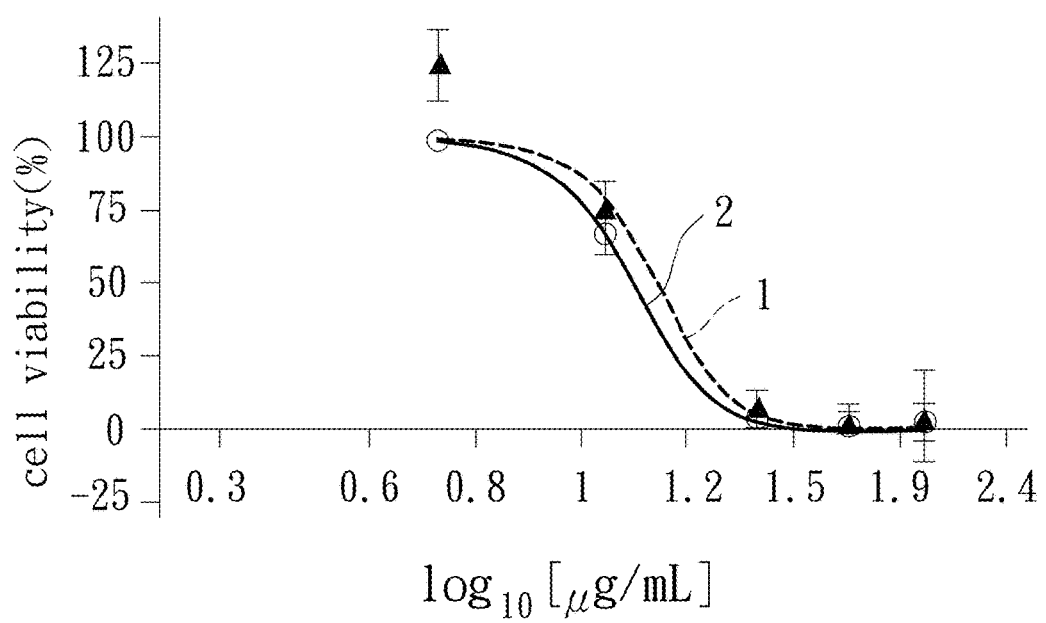
FIG. 13 is a bar chart illustrating cell viabilities of WPMY-1 and LNCaP under various dosage of an extract of *Asplenium nidus L.* in the present invention.

With reference to FIG. 13, the stromal myofibroblast-WPMY-1 (1) and the prostate cancer cell line-LNCaP (2) are cultured with a composite of the fractions b, c, and d, at various dosages respectively. After that, cell viabilities of the stromal myofibroblast-WPMY-1 and the prostate cancer cell line-LNCaP are determined after the culturation, by using colony formation assay. In FIG. 13, it is noted that the composite has inhibition against the growth of the stromal myofibroblast-WPMY-1 (see line 1) and the prostate cancer cell line-LNCaP (see line 2) in a dose-depended manner. Also, a higher dosage of the composite, such 100 µg/mL, will lead to the death of prostate cancer cells. In the present trial, the $IC_{50}$ of the composite on the stromal myofibroblast-WPMY-1 and the prostate cancer cell line-LNCaP 11.63 µg/mL and 13.19 µg/mL respectively.

Next, for proving the extract of *Asplenium nidus L.* in the preferable embodiment of the present invention truly having ability improving against androgen, a serial of trial is demonstrated below. However, the application of the said extract of *Asplenium nidus L.* is not limited to that.

C57BL/6Jnarl male mice purchased from the animal center of the National Laboratory Animal Center (NLAC, Taiwan) are used in this experiment. The mice are housed in a SPF animal room of Agricultural Biotechnology Research Center, Academia Sinica, Taiwan with constant temperature of 22° C. where is kept on a 12-hours light and 12-hours dark cycle.

BPH mice are induced by chronic $\alpha(1)$-adrenergic stimulation (15 mg/kg of body weight of the mice) and daily subcutaneous (sc) injection of phenylephrine (PE) 5 days/week for five weeks. Furthermore, the BPH mice are treated with different doses of the extract of *Asplenium nidus L.* of the invention. Prostate index (PI, ventral prostate wet weight/mouse weight), urine excretion and water intake of the BPH mice are recorded in FIGS. 14a, 14b and 14c. Moreover, the BPH mice are sacrificed and morphological aspects of ventral prostate are shown in FIG. 15.

Figure 14A:
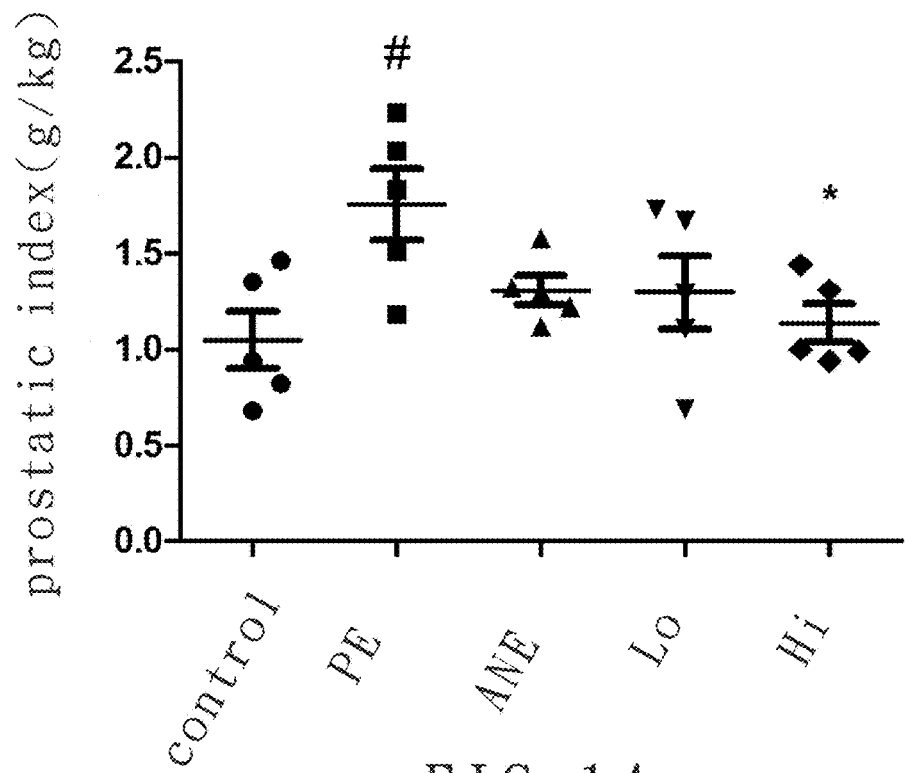
FIG. 14a is a chart illustrating prostatic index in BPH mice under various dosage of an extract of *Asplenium nidus L.* in the present invention.
Figure 14B:
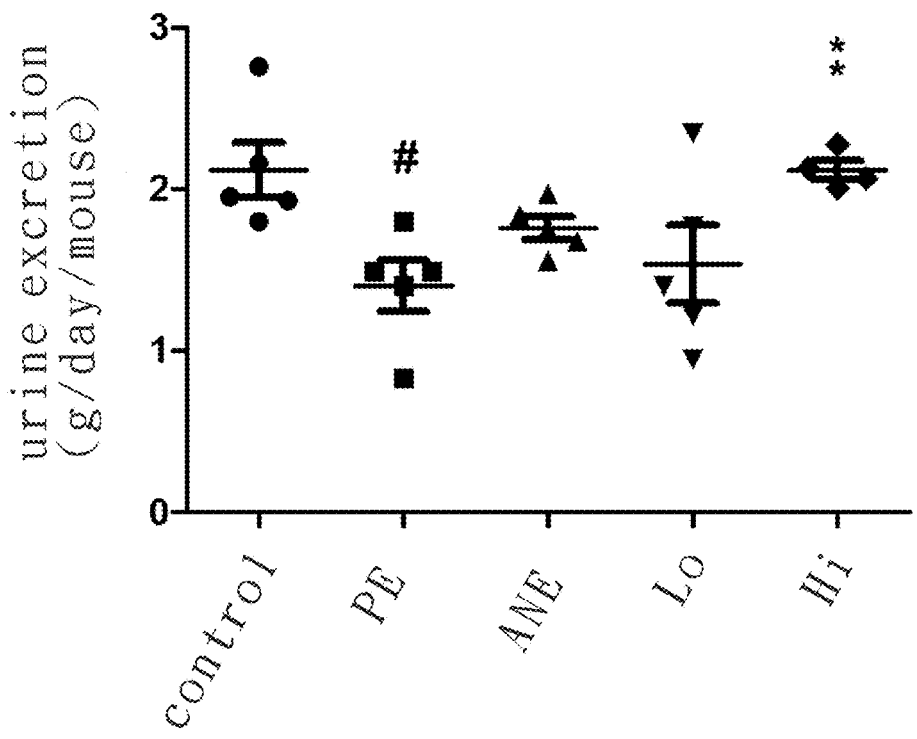
FIG. 14b is a chart illustrating excretion of urine in BPH mice under various dosage of an extract of *Asplenium nidus L.* in the present invention.
Figure 14C:
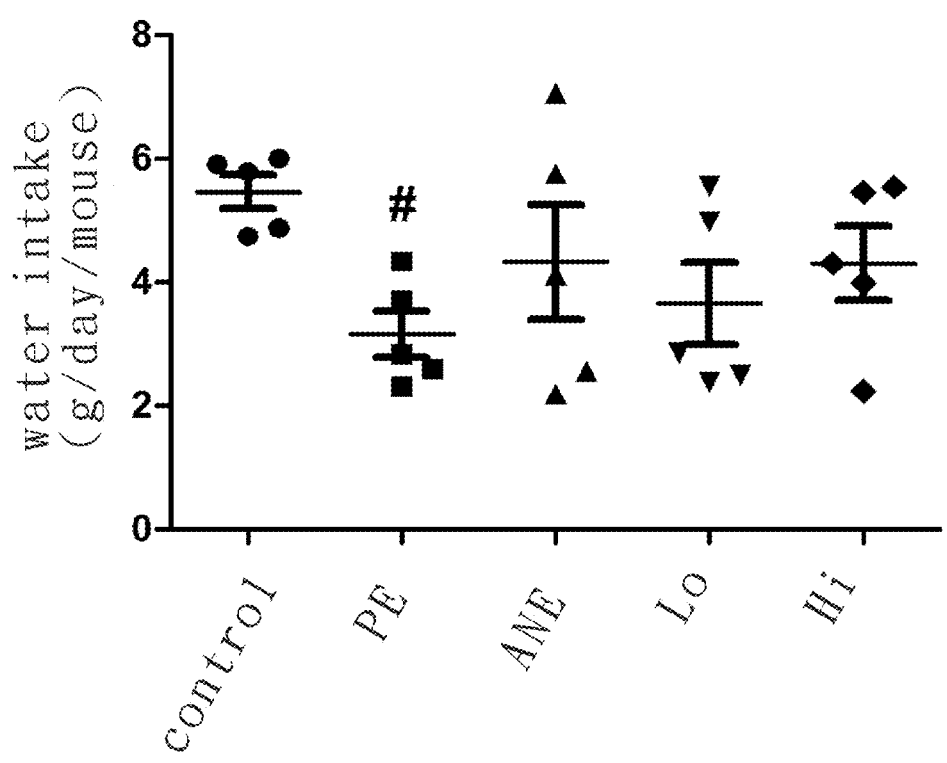
FIG. 14c is a chart illustrating water intake in BPH mice under various dosage of an extract of *Asplenium nidus L.* in the present invention.

As shown in FIG. 14a, compared with group control, group PE (treated with phenylephrine) has a significant increased PI value indicating the enlargement of prostate. The group PE excretes a significantly lower level of urine and an amount of water intake of group PE is significantly decreased over the group control. On the other hand, in group ANE (treated with ethanolic extract of *Asplenium nidus L.* without step of column chromatography, 100 mg/kg of body weight/day), group Hi (treated with the extract of *Asplenium nidus L.* of the invention, 50 mg/kg of body weight/day) or group Lo (treated with the extract of *Asplenium nidus L.* of the invention, 10 mg/kg of body weight/day), the PI, urine excretion and water intake return to the normal level ($p<0.01$, vs. PE group). The group Hi has a preferable effect if the PI, urine excretion and water intake (as shown in FIGS. 14a, 14b and 14c). As a result, the extract of *Asplenium nidus .* of the invention is capable of improving BPH phenomenon.

The groups control, PE, ANE, Lo and Hi are sacrificed and Hematoxylin-eosin staining (H&E staining) and Masson's trichrome staining of ventral prostate are preformed. In the H&E staining, compared with the group control, symptom of epithelial hyperplasia occurred in the group PE and the luminal areas of the ducts are decreased, suggesting a compression of secretory gland (as shown in FIG. 15-*ii*). The groups ANE, Lo and Hi are improved in the symptom of epithelial hyperplasia (as shown in FIG. 15-*iii, iv* and *vi*).

Figure 15:
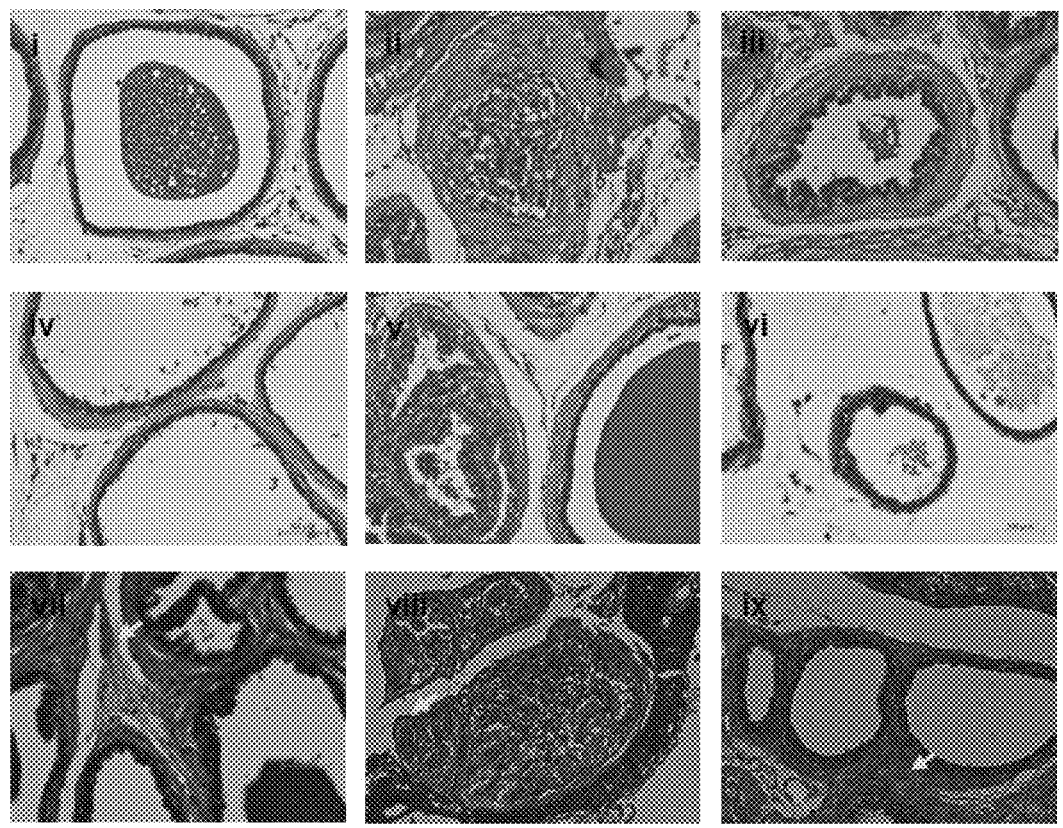
FIG. 15 is morphological aspects (to vi, H & E staining; Masson's trichrome staining, vii to ix, ×100) of the disease-free (i) & (vii), phenylephrine-stimulated (ii) and (viii), and samples-treated (iii: ANE; iv and v: Lo; vi and ix: Hi) ventral prostate in BPH mice under various dosage of an extract of *Asplenium nidus L.* in the present invention.

As shown in FIG. 15-*vii-xi*, collagen distributions of each group are shown in the Masson's trichrome staining. The group control (FIG. 15-*vii*) shows higher area of collagen (blue area, yellow arrows) and reticular fibers in the stromal region (orange arrows) than the group PE (FIG. 15-*viii*). Treated with the extract of *Asplenium nidus L.* of the invention (the group Hi) presents the restoration of collagen area and reticular fibers (FIG. 15-*ix*).

Therefore, the extract of *Asplenium nidus L.* of the invention is capable of improving PE-indued BPH phenomenon, increasing urine excretion and further improving the pathological characteristics of BPH. The extract of *Asplenium nidus L.* of the invention can be used as an active substance in a form of drug or healthy product treating of prostate disease.

Further, a practical example of the said extract of *Asplenium nidus L.* is provided below. However, the practical use of the said extract of *Asplenium nidus* . is not limited to that.

In the present trial, the said extracting method is carried out by processing the step of selection S3, the step of solvent extraction S1, and the step of column chromatography S2 sequentially, to extract the sample of *Asplenium nidus L.* and to obtain the extract of *Asplenium nidus L.* With reference to Table 1, the obtained extract of *Asplenium nidus L.* is given to 88 patients (in various age groups) that suffer from various prostate diseases (including benign prostate hyperplasia, prostate cancer or prostatitis). Obviously, the extract of *Asplenium nidus L.* is sufficient to be used on the therapy of benign prostate hyperplasia, prostate cancer and prostatitis, with symptoms of urination being improved in 2-4 weeks in average and without leading to any side effects.

Generally, one of primary symptoms of benign prostate hyperplasia is urorrhagia and nocturn. However, with treatment of the said extract of *Asplenium nidus L.*, frequencies of urophagia and nocturnal enuresis on patients are dramatically reduced till the same as normal. Moreover, according to International Prostate Symptom Score (I-PSS), the said 88 patients has around 20-30 points of improvement in 2-4 weeks. In comparison with other commercial health products (comprising 6% lycopene), only 2-3 points of improvement can be achieved.

TABLE 1

Therapeutic Effects on 88 Patients

| Ages | Effects | Numbers |
|---|---|---|
| 93~101 | Normal urination, do not need further treatment | 1 |
| 70~85 | Normal urination, do not need further treatment | 8 |
| 45~80 | Normal urination | 69 |
| | Normal urination, levels of PSA reduce from 8~9.5 to 6.0 in a short time | 2 |
| 55 | Normal urination in three days | 1 |
| 55~60[a] | Urination being fully recovered in 1-3 days | 2 |
| 60 | Frequency and velocity of urination turning normal | 1 |
| 70[b] | A great improvement on prostate | 1 |
| 60~70[c] | Fully recovering in 2 months | 3 |

[a]Patients having urinary tract adhesions (atypical symptom after prostate cancer surgery) after laser surgery. Urinary tract adhesions will last several months, and a general drug thereof is α-blocker. Instead, the extract of *Asplenium nidus* L. of the preferable embodiment in the present invention fast response to affect parts, effectively improving symptoms of urinary tract adhesions.
[b]A prostate cancer patient
[c]Patients of benign prostatic hyperplasia In summary, the extract of *Asplenium nidus L.* in the preferable embodiment of the present invention has natural active substances against androgen, and therefore, the said extract of *Asplenium nidus L.* is sufficient to be used on the therapy of diseases caused by hormone imbalance, prostate diseases (including benign prostate hyperplasia, prostate cancer and prostatitis) in particular. Also, the said extract of *Asplenium nidus L.* will not lead to any side effects to patients. The said extract of *Asplenium nidus L.* is easily to obtain via a convenient extracting method, and which is capable of being further applied to therapy or prophylaxis of the prostate disease, as an active substance in medications or health products thereof, to improve males' prostate issues.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A method of treating benign prostate hyperplasia in a subject in need thereof comprising:
    administering an effective amount of an extract of *Asplenium nidus L.* to the subject, wherein the extract comprises:
        pyropheophorbide a methyl ester;
        pheophorbide a methyl ester;
        1-linleoyl-3-linolenoyl-glycerol;
        1-linleoyl-2,3-dipalmitoyl-rac-glycerol; and
        1,3-dipalmitoyl-sn-glycerol.

2. The method as claimed in claim 1, wherein the extract of *Asplenium nidus L.* is in the form of a health product.

3. The method as claimed in claim 1, wherein the effective amount of the extract of *Asplenium nidus L.* is 10-50 mg/kg of body weight of the subject in need thereof.

4. The method as claimed in claim 1, wherein the effective amount of the extract of *Asplenium nidus L.* is 50 mg/kg of body weight of the subject in need thereof.

5. A method of treating prostatitis in a subject in need thereof comprising:
    administering an effective amount of an extract of *Asplenium nidus L.* to the subject, wherein the extract comprises:
        pyropheophorbide a methyl ester;
        pheophorbide a methyl ester;
        1-linleoyl-3-linolenoyl-glycerol;
        1-linleoyl-2,3-dipalmitoyl-rac-glycerol; and
        1,3-dipalmitoyl-sn-glycerol.

6. The method as claimed in claim 5, wherein the extract of *Asplenium nidus* . is in the form of a health product.

7. The method as claimed in claim 5, wherein the effective amount of the extract of *Asplenium nidus L.* is 10-50 mg/kg of body weight of the subject in need thereof.

8. The method as claimed in claim 5, wherein the effective amount of the extract of *Asplenium nidus L.* is 50 mg/kg of body weight of the subject in need thereof.

\* \* \* \* \*